US010182797B2

(12) United States Patent
Holzer

(10) Patent No.: US 10,182,797 B2
(45) Date of Patent: Jan. 22, 2019

(54) MULTI-FUNCTION DERMATOLOGICAL BIOPSY INSTRUMENT

(71) Applicant: Aton Holzer, Boca Raton, FL (US)

(72) Inventor: Aton Holzer, Boca Raton, FL (US)

( * ) Notice: Subject to any disclaimer, the term of this patent is extended or adjusted under 35 U.S.C. 154(b) by 711 days.

(21) Appl. No.: 14/817,793

(22) Filed: Aug. 4, 2015

(65) Prior Publication Data
US 2016/0058431 A1   Mar. 3, 2016

Related U.S. Application Data

(60) Provisional application No. 62/032,705, filed on Aug. 4, 2014.

(51) Int. Cl.
| | | |
|---|---|---|
| *A61B 10/02* | (2006.01) | |
| *A61B 17/00* | (2006.01) | |
| *A61B 17/064* | (2006.01) | |
| *A61B 17/068* | (2006.01) | |
| *A61B 90/00* | (2016.01) | |
| *A61B 17/06* | (2006.01) | |

(52) U.S. Cl.
CPC .... *A61B 10/0266* (2013.01); *A61B 17/00491* (2013.01); *A61B 17/064* (2013.01); *A61B 17/068* (2013.01); *A61B 90/39* (2016.02); *A61B 2010/0208* (2013.01); *A61B 2017/00004* (2013.01); *A61B 2017/0641* (2013.01); *A61B 2017/0647* (2013.01); *A61B 2017/0649* (2013.01); *A61B 2017/06176* (2013.01); *A61B 2090/395* (2016.02); *A61B 2560/0418* (2013.01)

(58) Field of Classification Search
CPC .......... A61B 10/0266; A61B 17/00491; A61B 17/064; A61B 90/39; A61B 17/068; A61B 2017/0649; A61B 2090/395; A61B 2017/0647; A61B 2017/0641; A61B 2017/06176; A61B 2010/0208; A61B 2560/0418

See application file for complete search history.

(56) References Cited

U.S. PATENT DOCUMENTS

| | | | | |
|---|---|---|---|---|
| 3,515,128 | A * | 6/1970 | McEvoy | A61B 10/02 30/130 |
| 4,461,305 | A * | 7/1984 | Cibley | A61B 10/0266 30/113.1 |
| 5,089,009 | A * | 2/1992 | Green | A61B 17/064 411/457 |
| 5,192,270 | A * | 3/1993 | Carswell, Jr. | A61M 5/178 604/116 |

(Continued)

*Primary Examiner* — Rene T Towa
(74) *Attorney, Agent, or Firm* — Israel Nissenbaum; Yitzy Nissenbaum

(57) ABSTRACT

A method for effecting a dermatological biopsy procedure and a hand-held instrument for use in such procedure. The instrument has a pen-like housing with an aperture and a biopsy site marker. A syringe for dispensing an anesthetic to a selected marked biopsy site on a patient's skin and a biopsy-sampling blade such as a skin punch or scraper and a wound closure device for closing the biopsy wound with a suture, adhesive or cauterant are contained within the housing. The aperture of the instrument is placed directly against the marked biopsy site and the syringe, biopsy blade and wound closure device are controlled to alternately extend and retract through the aperture and operatively effect anesthetic dispensing, biopsy sampling and wound closure.

16 Claims, 7 Drawing Sheets

(56) References Cited

U.S. PATENT DOCUMENTS

| | | | |
|---|---|---|---|
| 6,312,412 B1* | 11/2001 | Saied | A61M 5/20 604/191 |
| 6,547,467 B2* | 4/2003 | Quintero | A61B 17/00491 206/438 |
| 2007/0232954 A1* | 10/2007 | Harris | A61B 10/02 600/564 |
| 2009/0253998 A1* | 10/2009 | Chen | A61B 10/0266 600/565 |
| 2011/0282240 A1* | 11/2011 | Al Mohizea | A61B 10/0233 600/566 |
| 2012/0265096 A1* | 10/2012 | Mendez-Coll | A61B 10/0233 600/567 |
| 2013/0172777 A1* | 7/2013 | Kwon | A61B 10/0283 600/566 |
| 2013/0324910 A1* | 12/2013 | Ohri | A61B 10/0233 604/21 |

* cited by examiner

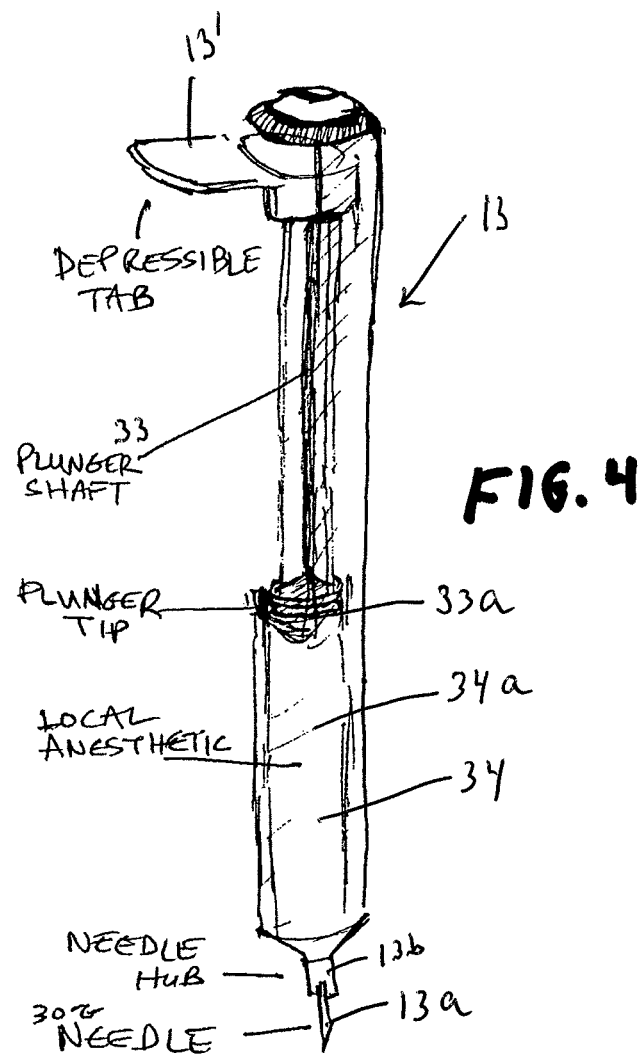

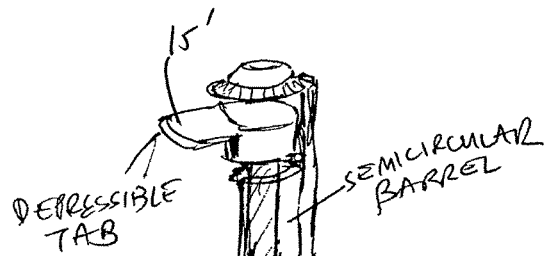
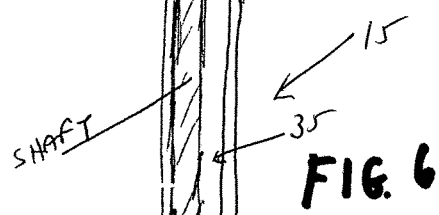
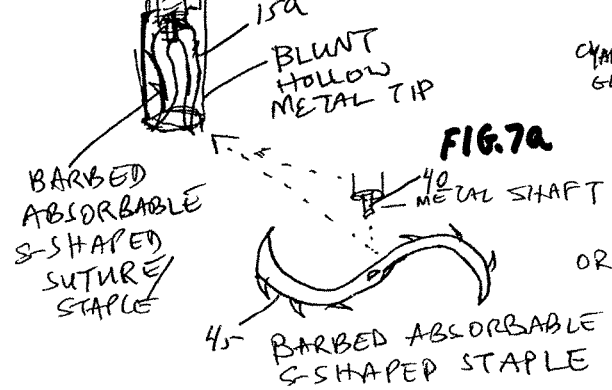
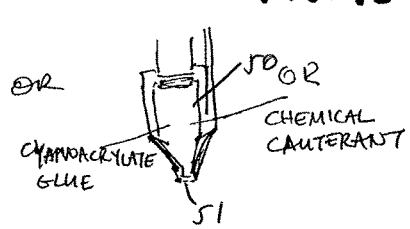

MULTI-FUNCTION DERMATOLOGICAL BIOPSY INSTRUMENT

FIELD OF THE INVENTION

This invention relates to instruments used in effecting or carrying out dermatological biopsies and in particular relates to instruments providing multiple biopsy functions.

BACKGROUND

A dermatological or skin biopsy procedure, such as for determining skin cancer and the like, involves certain general procedures, which are often effected by different instruments. A typical biopsy procedure entails the initial marking of the biopsy site with a visible marker. Thereafter, the marked site is injected with a local anesthetic, typically lidocaine. A skin removal device, for the typical removal of a skin sample of between 3-5 mm is used for obtaining the sample for biopsy (most commonly 4 mm). Such skin removal devices are commonly of two types, a skin scraper for removal of a shallow skin sample, and a skin punch, which cores a skin sample of greater depth. Use of the skin punch requires further measures for wound closure such as suturing or cauterizing of the punch wound. Because of the shallower depth of skin removal by the skin scraper, wound closure with a suture may or may not be required, depending on the nature of the biopsy wound.

Separate instruments are often used for each of the aforementioned procedures with complications engendered thereby. Often, the proper following of the procedures requires several people to perform the steps. This further often necessitates the need for coordination as well as proper and exact positioning of the instruments of anesthetic and biopsy removal to provide for minimal time for the procedure with the greatest accuracy in biopsy sample taking and with minimal patient pain and most effective healing measures.

In an example of the above, punch biopsy of the skin is a procedure by which dermatologists obtain tissue for histopathologic evaluation. The procedure as currently done requires several components. The dermatologist who wishes to perform the punch biopsy must incise the skin, and then drop the obtained tissue sample into an open specimen bottle. For effective handling, the dermatologist must generally have an assistant on hand to assist.

This procedure is however, not staff-efficient, since it requiring an assistant to draw anesthetic, to prepare instruments on a tray and to cut the suture. In addition, pitfalls of the current technique include often-happening occurrences wherein:
  (1) the biopsy specimen detaches during the punch incision and becomes lodged in the coring blade, requiring ingenuity to remove it;
  (2) when the biopsy specimen does not detach with the punch incision, removal with forceps can crush the specimen and create difficulties for the interpreting dermatopathologist for proper diagnosis.

Furthermore, the typical use of suture closures, obligates the patient to return in a week's time for suture removal, even if the pathologic diagnosis (and hence follow-up visit) may be available sooner. Although placement of an absorbable subcutaneous suture would obviate the need for this return visit, common absorbable sutures are generally impractical in the 4-mm hole created by the most common size of punch biopsy device.

SUMMARY

It is accordingly an object herein to provide a single multi-function biopsy instrument for the taking of skin samples, which permits single-person operation with increased efficiency and accuracy of coordinating anesthetic dosing and skin removal site and optionally with skin biopsy wound closure such as with suturing which does not require suture removal.

It is a further object is to provide a biopsy system that facilitates injection of anesthetic, removal and ejection of obtained biopsy specimens and wound closure by means of one disposable device, resolving many, if not all, of the inefficiencies and pitfalls of common prior art procedures.

An instrument for use in a dermatological biopsy sampling procedure as disclosed herein comprises a hand-held device comprising:
  a) a member configured for effectively dispensing an anesthetic to a selected biopsy site on a patient's skin, and
  b) a member configured for taking a biopsy sample from the biopsy site.

The instrument comprises a housing for the anesthetic dispensing member and biopsy sample taking member with the housing having an aperture therein adapted to be placed into contact directly against the biopsy site. The instrument comprises an extension and retraction mechanism configured to enable the anesthetic dispensing member and biopsy sample taking member to be alternately brought into proximate position relative to the selected biopsy site through the aperture. This enable the alternate and sequential providing of an anesthetic to the selected biopsy site and to take a biopsy sample from the anesthesized biopsy site, respectively, without necessity for removal of the instrument from contact with the biopsy site. This facilitates single user operation and accuracy biopsy site sampling.

In a useful embodiment the housing further contains:
  i) a member configured to hold, apply and control an element for closure of a wound caused by the taking of the biopsy sample, and
  ii) the extension and retraction mechanism being further configured to enable the wound closure member to be alternately, relative to the biopsy sample taking member, brought into proximate position relative to the biopsy wound through the aperture to close the wound with the element for closure A further embodiment herein comprises a single use multi-function biopsy instrument in a pen-like configuration comprising an anesthetic dispensing member with a dispensing activating element and a skin biopsy sampling member with a sample taking control element. Each of the anesthetic dispensing member and skin biopsy sampling member comprises an advancing and retracting mechanism configured for the alternating positioning and operative functioning of the anesthetic dispensing member and the skin biopsy sampling member at a single skin site without the necessity of moving the instrument out of a single position placement, for effecting the skin biopsy sampling. The single site placement of the anesthetic dispensing and the biopsy sampling ensures greater accuracy, expedited handling and reduced possibility of patient pain.

For further enhanced expediency, the instrument may also integrally contain a site marking element or marker and an integral suturing member, with the latter, in one embodiment, being provided with its own advancing and retracting mechanism and operational manipulating suturing element. The advancing and retracting mechanism of the integral suturing member, when part of the device, is further alternated with the positioning of the other functional members used in the biopsy sampling procedure.

In an embodiment of the instrument herein, the integral suturing element positions and operationally rotationally sets a surgical suture with a barbed absorbable staple configuration. In an embodiment of the instrument, the marking element is contained within a cap for the biopsy pen instrument and the anesthetic dispensing member, skin biopsy sampling member and the integral suturing member, when present, are longitudinally positioned and arranged within a cylindrical barrel having a tapered open end, similar to that of a pen, through which the respective members are extended to effect the respective functions of anesthetic delivery, skin biopsy sampling and optional suturing. Suturing, if required, may be effected by a separate suturing instrument and its inclusion in the instrument herein is desirable though not necessary.

In another embodiment of the invention a device is provided that contains:
1) a surgical marker,
2) local anesthetic syringe,
3) coring blade with an undercutting blade and ejector mechanism, and
4) an absorbable suture or staple that can be lowered into the wound.

The device described herein allows the hurried practitioner to easily perform a punch or scraping biopsy procedure without the need for assistants. It also ensures the easy removal of the specimen from the coring or scraping blade and removes the possibility of a crushed artifact. Additionally, with the integral suturing element, placement of the absorbable suture or staple obviates the need for a return visit for suture removal.

The above described instrument is used in effecting a biopsy sampling procedure in a method embodiment in which:
a dermatological biopsy sample is obtained from a patient's skin with the steps of:
a) marking a selected biopsy sampling site;
b) placing the aperture of the hand-held instrument of claim 12 in direct proximate contact with the marked selected biopsy sampling site;
c) advancing the anesthetic containing syringe needle through the aperture and injecting the marked selected biopsy site with the anesthetic;
d) without removal of the instrument from the selected biopsy site, retracting the syringe needle from the aperture and advancing the biopsy sample taking member through the aperture and cutting a biopsy skin sample from the anesthesized biopsy site;
e) retaining the biopsy skin sample for sample removal from the instrument;
f) retracting the biopsy taking member from the aperture and advancing the biopsy wound closure member through to aperture and closing the biopsy wound; and
g) removing the biopsy skin sample from the instrument either before or after the closing of the biopsy wound.

Additional objects, features and advantages of the invention will become more evident from the following discussion and drawings in which:

SHORT DESCRIPTION OF THE DRAWINGS

FIG. 4 is a front perspective view of the anesthetic delivery cartridge shown in FIGS. 2 and 3, taken apart from the instrument;

FIG. 6 is a front perspective view of the suturing cartridge shown in FIGS. 2 and 3, taken apart from the instrument;

Figure 1:
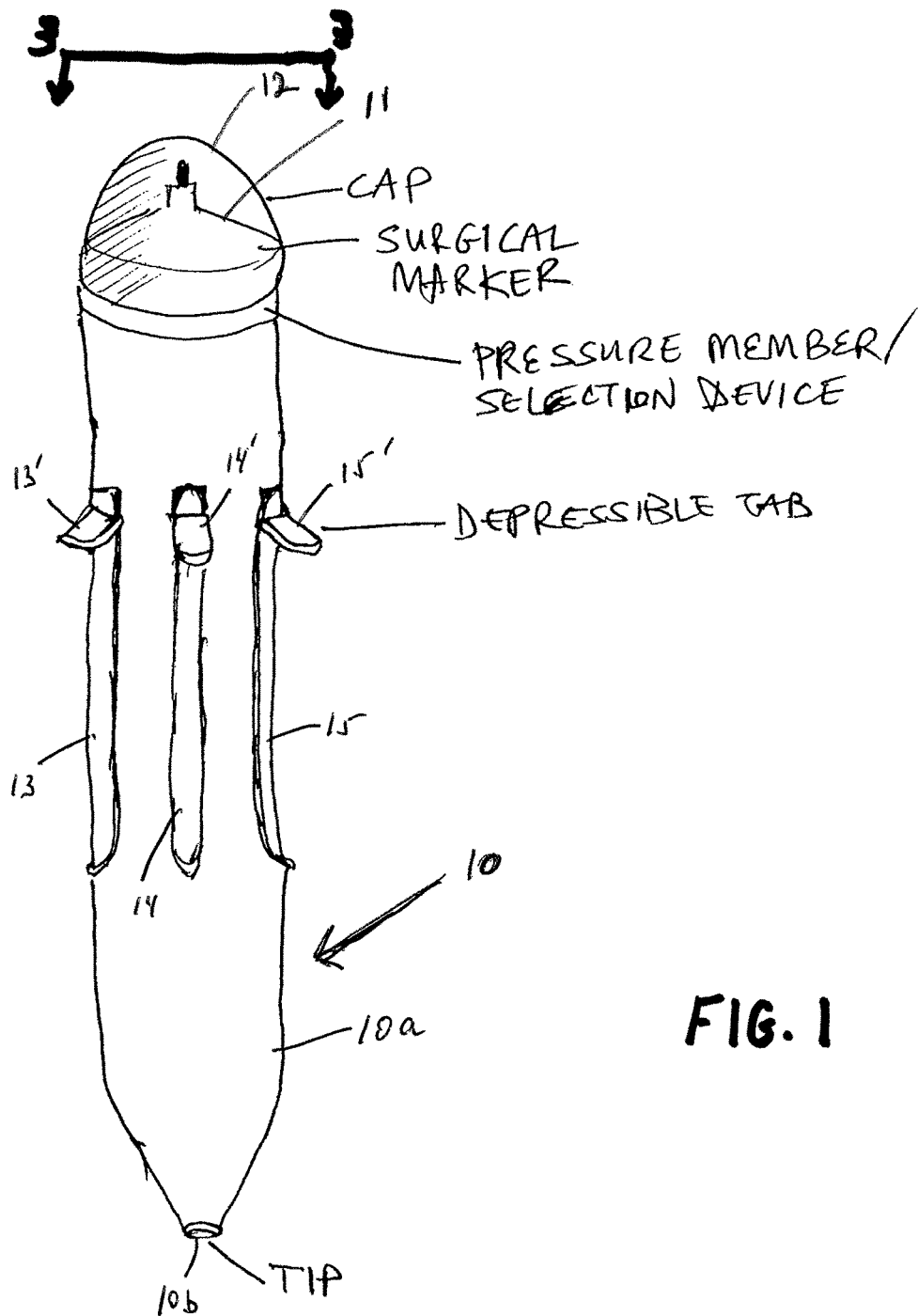
FIG. 1 is a front view of an embodiment of the multifunction biopsy instrument of the present invention with control tabs all shown in front for clarity.
Figure 2:
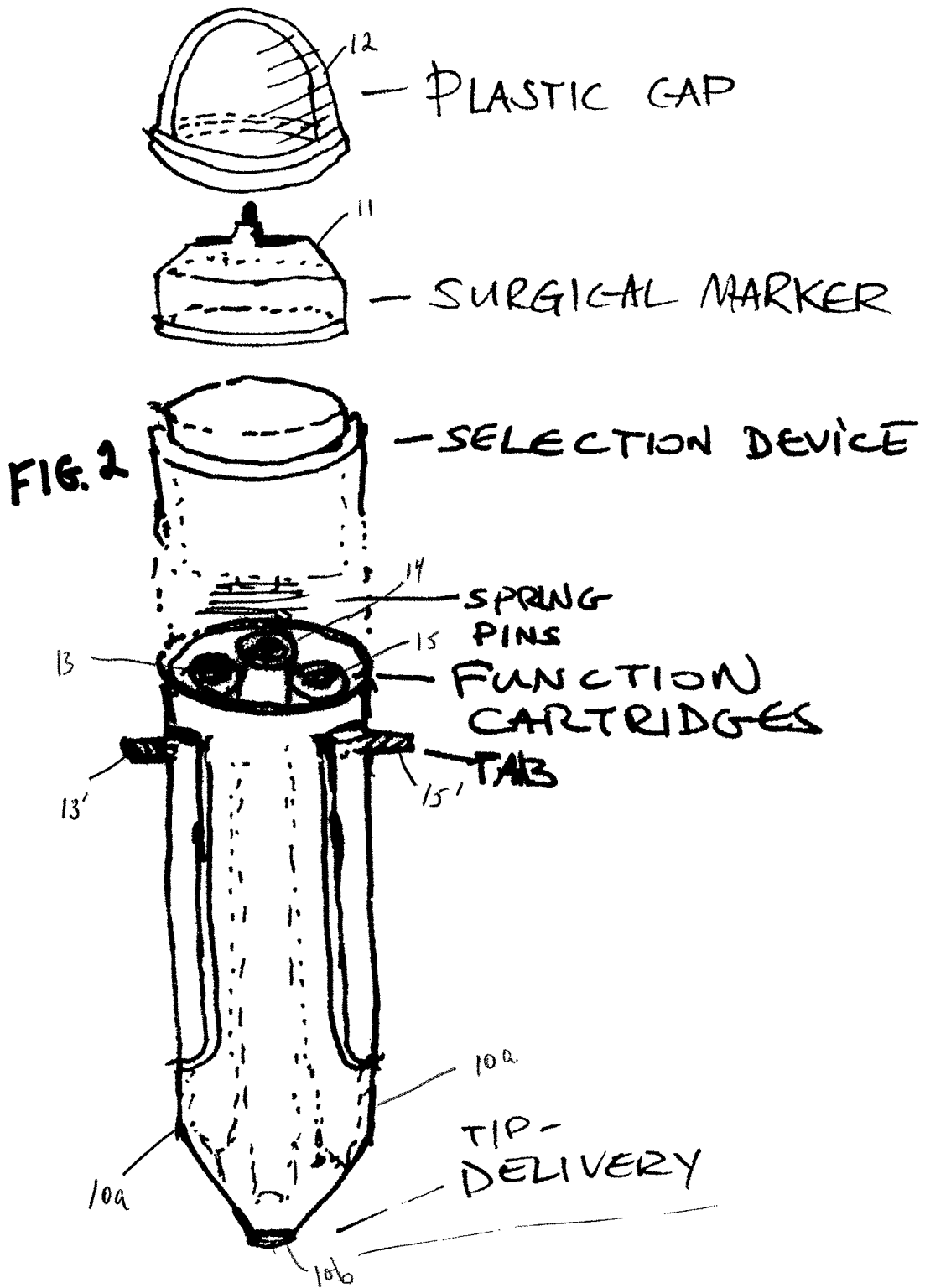
FIG. 2 is an exploded view of the multi-function biopsy instrument of FIG. 1.
Figure 3:
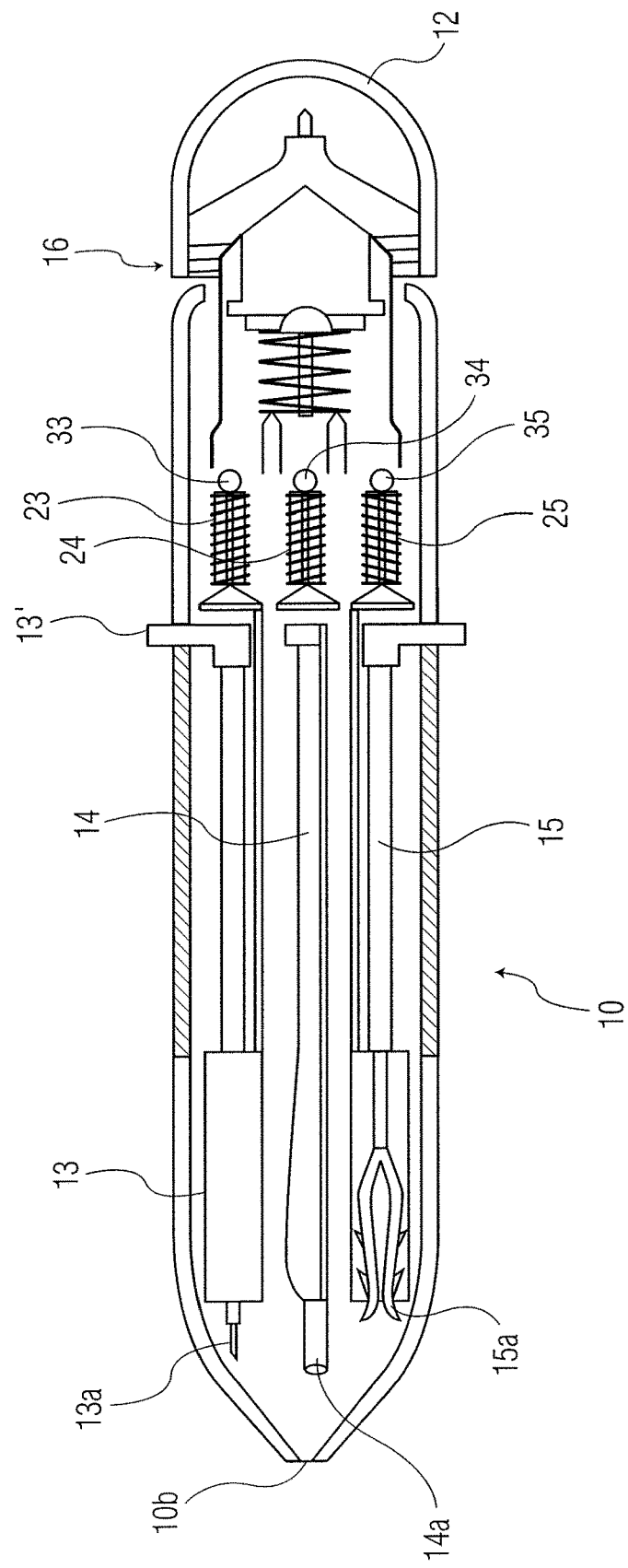
FIG. 3 is a sectioned view of the multi-function biopsy instrument of FIG. 1 taken along line 3-3.
Figure 8:
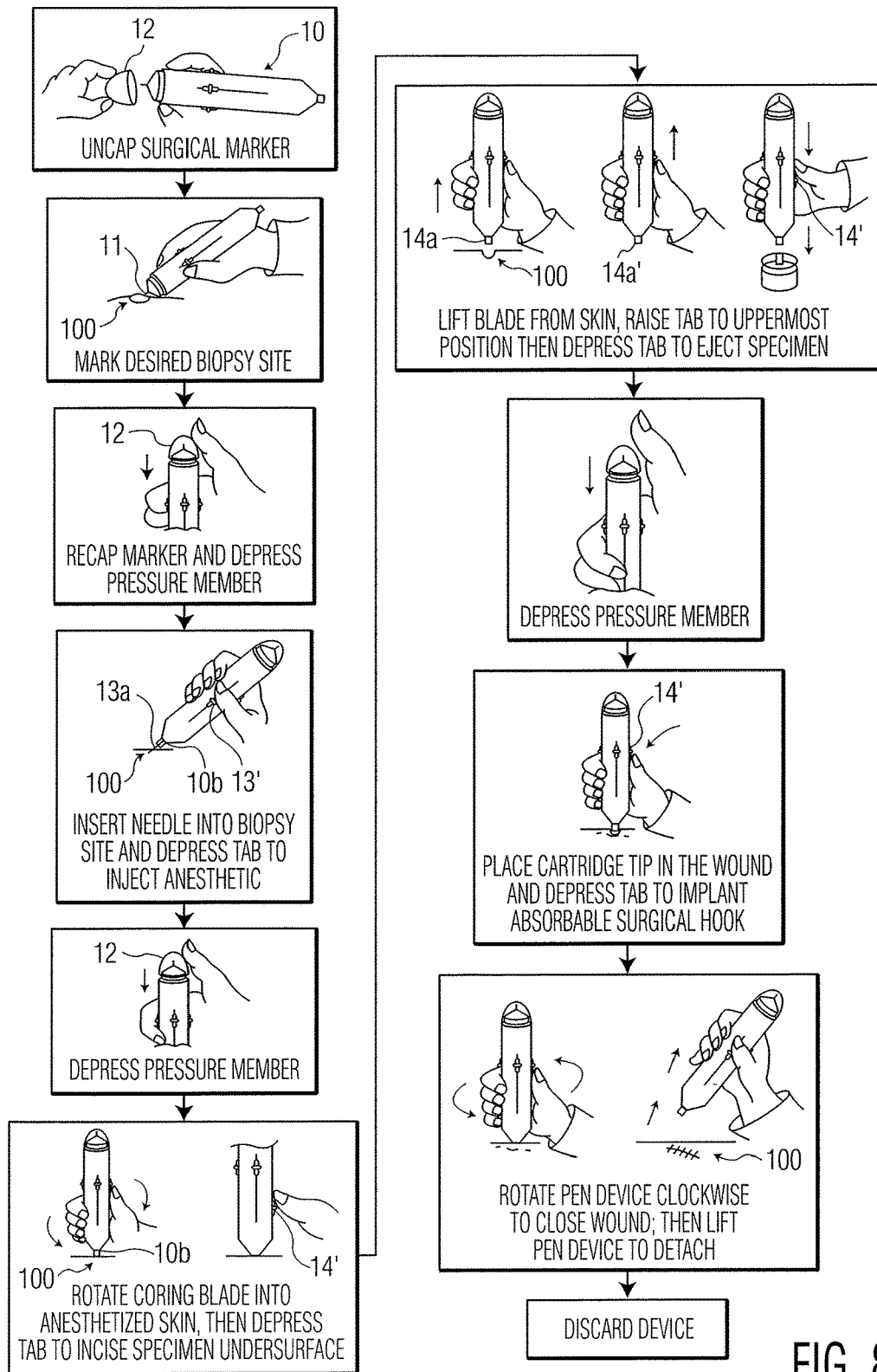

FIGS. 7a-d are suturing alternatives of an s-shaped barbed absorbable staple, a three pronged suture, a barbed helical suture, and a cyanoacrylate glue dispenser or chemical cauterant, as used with or integrated with the suturing cartridge tip of the suturing cartridge of FIG. 6: and FIG. 8 is an illustrated flow chart showing the procedure of using the multi-function instrument of FIGS. 1-3 in effecting a biopsy sampling use.

DETAILED DESCRIPTION AND DESCRIPTION OF DRAWINGS

According to some exemplary but not limiting embodiments, a multifunction pen type device for skin biopsy comprises three cartridges, which are individually selectively advanceable to the tip of the device and are substantially completely retractable into the body of the device.

In some embodiments, as described above, less than three or more than three cartridges are optionally used, with space therefor being modified, if necessary, in the instrument. In some embodiments, a pressure element is biased under spring action or other bias device to bring the respectively chosen function cartridge into the use position, and then returned into the rest or storage position by means of intermediate members.

In an embodiment, a plurality of pins which carry the different function cartridges are displaceable in the lower part of a housing. Arranged above these are swingable push rods actuable by means of pressure elements, which co-act with the respective underlying cartridge carrying pins in, for example, a diagonal or horizontal position. A displaceable pressure pin may be used for choosing, advancing and retracting the function cartridge, which is under the influence of a conical spring or other bias device arranged in a bushing threaded into the casing in operating position and in the rest position, with a control pendulum mounted on the spring longitudinally limited thereby and rotatable therein. In addition, a guide part is positioned at the forward end of the casing with a cartridge-bearing pin longitudinally displaceable in the longitudinal bores of the guide part under the influence of coil springs and provided with joints at its rear end and a locking guide ring positioned at the guide part. Other cartridge selection mechanisms may optionally be used.

In a useful embodiment, once advanced into place, each cartridge is equipped with a depressible tab that completes its function. The three cartridges include a syringe containing a local anesthetic, which can be injected by depressing its tab; a coring blade for punch biopsy, equipped with a curving blade at one lateral aspect that can be lowered via the depressible tab to incise the base of the specimen and enclose it within the coring blade, and, when subsequently raised to a height above the coring blade, enters the coring blade from above so that it can be lowered to eject the collected specimen; and a tube containing an S-shaped barbed absorbable surgical hook, or a three- (or more) armed surgical hook, or an absorbable suture or barbed helical suture that, when lowered into the wound, can be twisted and detached to achieve wound closure. Another embodiment may have, in place of the cartridge with coring and curving blades, a scoop-like blade and barrel to perform a shave biopsy, and in place of the cartridge containing the absorbable hook, a cartridge containing chemical cauterant, or cyanoacrylate glue. Another embodiment could incorporate a fourth cartridge with a tattoo needle and either permanent or temporary UV-fluorescent tattoo ink to provide a mark of the biopsy site for the purpose of future identification of the biopsy site of a skin cancer. In some embodiments, a gentian violet surgical marking pen is incorporated into the push button at the base of the device.

In operation, according to some embodiments, the user uncaps the surgical marker and uses it to draw a circle around the desired punch location. The push button is depressed, advancing the syringe of anesthetic to the tip of the device. Depression of the depressible tab of the syringe injects anesthetic into the desired site. The push button when depressed again, advances the coring blade to the tip of the device. The practitioner rotates the coring tip into the skin to create the incision, and advances the tip to its hub. Depression of the depressible tab of the coring blade cylinder to its lowermost point advances the curved blade to below the space of the coring blade, and the user rotates the device to incise the entire base of the specimen. The device is then lifted, pulling the specimen out of the skin. The user positions the device above a specimen bottle, raise the depressible tab to its highest point to position the curved blade above the coring blade, and depresses the depressible tab, pushing the flat end of the curved blade into the coring blade, to serve as a piston to eject the specimen into the bottle. The push button is then depressed for the third time, advancing the tube containing the S-shaped surgical hook. The tube is inserted into the wound, and the tab depressed to lower the surgical hook into the base of the wound. The user twists the device to close the wound, and then lifts the device off of the wound to detach the S-shaped hook, completing the biopsy and closure. In some embodiments, separate activation devices and/or push buttons may be provided for each cartridge and/or function. In an alternative embodiment, since the device is for single use, the specimen is retained in a receptacle integrated with the coring or scraping element and the receptacle is removed in toto for retrieval of the specimen in a fully intact state.

With specific reference to the drawings, FIGS. 1-3 depict views of the biopsy pen 10, with a surgical marker 11, contained within cap 12 and in exploded and cross sectioned views respectively. The operational cartridges 13, 14 and 15; of anesthetic delivery syringe 13, biopsy sampling (coring and scraping) element 14 and suturing element 15, are longitudinally positioned within pen barrel 10a, with their operational elements (of anesthetic dispensing needle 13a; coring blade 14a, curved scraping blade 14b; and surgical suture holder 15a), being directly adjacent pen aperture tip 10b, for alternative operational extension therefrom. Logistically, the specific instrument being used is provided with either the coring or scraping blade for more specific operation control, though both biopsy removal blades may be selectively included with appropriate mechanism for selection such as with separate cartridge elements.

The pen barrel 10a is further provided with cartridge selection control device 16 for selection and extension/retraction control of the cartridge appropriate for a desired function. Control tabs 13', 14' and 15', integrated with cartridges 13, 14 and 15 respectively (as shown in FIGS. 4, 5, and 6 respectively), serve to effect the appropriate function of the desired cartridges (injection, scraping or coring, and suturing). Internal springs 23, 24 and 25 with pins 33, 34, and 35 for cartridges 13, 14 and 15 respectively provide requisite position and operation tension forces for the extension/retraction of the selected respective cartridges.

For the selective positioning of the operation tips 13a, 14a and 14b and 15a, they are held in an offset position relative to the aperture tip 10b until extended for use and with such extension are moved into alignment with the aperture tip 10b and therethrough for effecting the designated function.

FIG. 4 depicts the anesthetic needle dispenser cartridge 13, apart from the pen structure, with control tab 13', plunger shaft 33, plunger tip 33a, anesthetic ampoule 34 with contained anesthetic 34a, needle hub 13b and needle 13a.

Figure 5A:
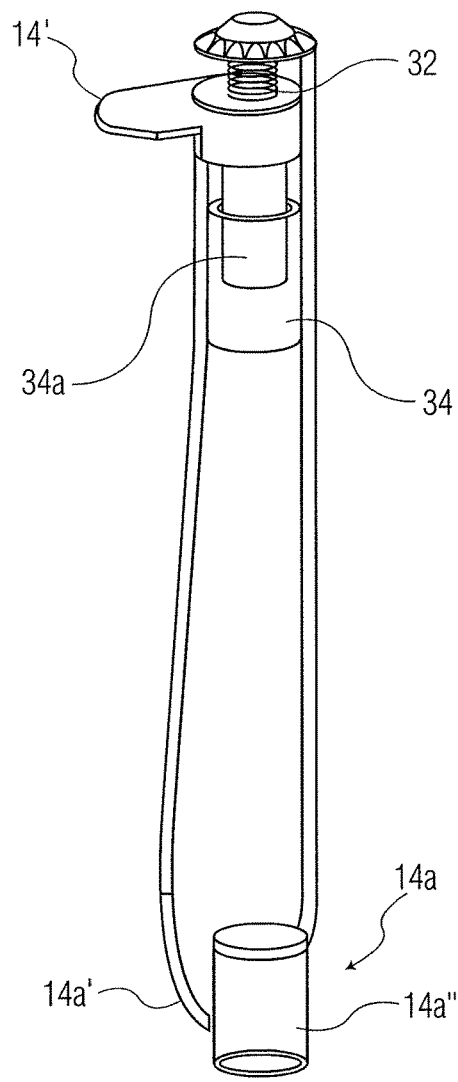
FIGS. 5a and 5b is a front perspective view of the skin biopsy sampling cartridge shown in FIGS. 2 and 3, taken apart from the instrument with FIG. 5a showing a coring blade and FIG. 5b showing an alternative operational shave blade.
Figure 5B:
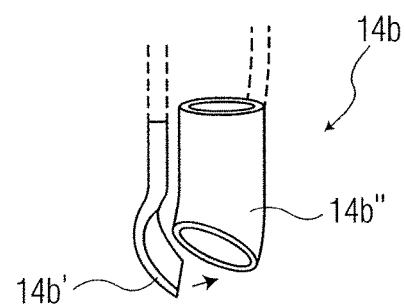

FIGS. 5a and 5b show the biopsy sample obtaining structure 14, with spring 32, plunger barrel 34 and plunger tip 34a and control tab 14'. The biopsy tip 14a in FIG. 5a comprises a curved blade 14a' and coring blade 14a". The biopsy tip 14b in FIG. 5b shows the alternative shave biopsy mechanism with sharp scoop blade 14b' and blunt edge receptacle 14b".

The optional suturing cartridge 15 is shown in FIG. 6 with control tab 15' driving shaft 35 longitudinally contained and movable within semicircular barrel 36 to operate blunt hollow tip 15a engaged with one of barbed absorbable sutures shown in FIG. 7a (s-shaped staple 45), FIG. 7b (3-pronged suture 46) and FIG. 7c (barbed helical suture 47) via metal shaft connector 40 of hollow tip 15a for rotational suturing deployment to close a biopsy wound. Alternatively, tip 15a is shaped with a small ampoule configuration 50 containing a medical grade cyanoacrylate glue or chemical cauterant which is dispensed on the biopsy wound site through dispensing tip 51 to effect a biopsy wound closure without sutures.

As shown in illustrated flow chart of FIG. 8 of an operational procedure utilizing the biopsy instrument 10, the cap 12 is initially removed at A and the marker 11 is used to mark (with a small diameter circle) the biopsy site 100 at B. Thereafter, with the cap 12 having been replaced the cap is pressed at C to depress an internally contained pressure member, which initially causes the needle 13a of the anesthetic dispensing cartridge 13 to operationally extend out of tip opening 10b at D and the needle 13a is positioned into the marked biopsy site and tab 13' is depressed to inject anesthetic into the biopsy site 100.

Without lifting the instrument 10 from against the biopsy site 100, the cap 12 is then pressed again at E to depress the pressure member. This causes the biopsy-sampling cartridge 14 to move into position at F and in turn causes the tip 14a (with either coring tip 14a' or shaving tip 14a") to extend into engagement with the biopsy site 100. The biopsy instrument 10 is then rotated at G for coring or shaving and then the tab 14' is depressed to effect the coring or shaving incision under or on the skin surface at the biopsy site 100. Raising of tab 14' at H lifts the biopsy sample from the biopsy site with the sample being retained within the coring blade 14a" or blunt edge receptacle 14b" with the biopsy instrument 10 being lifted from the biopsy site 100. Depression of tab 14' thereafter, as shown, ejects the specimen for collection within receptacle 101.

To complete the procedure the biopsy instrument 10 is repositioned on the biopsy wound the cap 12 is again pressed to depress the pressure member at I to bring the suturing cartridge 15 into position and operative extension with suturing tip 15a. Tab 15' is depressed to implant the absorbable suturing staple (45, 46, or 47) or to dispense the cyanoacrylate glue or cauterant. The biopsy instrument 10 is then rotated to close the wound with any of the surgical staples, glue or cauterant and the biopsy instrument is lifter to detach it from the staple, glue or cauterant and the biopsy instrument is then discarded.

In another embodiment, ejection of the biopsy sample need not be made prior to the suturing step, with the biopsy instrument remaining in position against the biopsy site and wound 100 until after the suturing or wound closure has been effected and the biopsy sample being harvested with removal of the biopsy sample cartridge 14 and removal of the contained sample therefrom.

It is understood that the above description and drawings are merely illustrative of embodiments herein and that changes may be made in structure of the biopsy instrument and procedure for use thereof without departing from the scope of the invention except as defined in the following claims.

What is claimed is:

1. A multi-function manually manipulable biopsy sampling instrument for use in a dermatological biopsy sampling procedure comprising:
   a) a housing having an aperture in a base thereof, with the aperture adapted to be placed on a patient's skin, with a periphery of the aperture encircling a selected biopsy site of the patient's skin and wherein the periphery of the aperture is placed on the patient's skin, without removal of the instrument from the patient's skin, during the biopsy sampling procedure;
   b) retractable syringe with contained anesthetic, within the housing configured for effectively dispensing an anesthetic to the selected biopsy site on a patient's skin, after the aperture periphery is placed on the patient's skin;
   c) cutting or scraper blade, within the housing, configured for cutting or scraping a biopsy sample from the biopsy site, and
   d) a sample taking member, within the housing, configured for positioning between the cut or scraped biopsy sample and the patient and separating the biopsy sample from the anesthetized biopsy site for the removal of the biopsy sample from the patient;
   wherein the instrument comprises an extension and retraction mechanism, within the housing, configured to cause the retractable syringe, cutting or scraper blade and sample taking member to be held in an offset position relative to the aperture and to be alternately brought into proximate position, relative to the selected biopsy site, into alignment with the aperture for extension through the aperture, with each of the syringe and cutting or scraper blade being adapted to be sequentially extended, retracted and laterally moved to an offset position relative to the aperture to alternately and sequentially provide an anesthetic to the selected biopsy site and to cut or scrape a biopsy sample from the anesthetized biopsy site and to enable separating of the biopsy sample from the anesthetized biopsy site, respectively, without removal of the instrument from contact with the patient's skin peripheral to the biopsy site.

2. The biopsy sampling instrument of claim 1, wherein the housing further contains:
   e) a wound closure dispenser configured to hold, apply and control a skin retention element for closure of a wound caused by the taking of the biopsy sample, and the extension and retraction mechanism being further configured to enable the sample taking member to laterally move to the offset position relative to the aperture to enable the wound closure dispenser to be alternately, brought from an offset position relative to the aperture into proximate extending position through the aperture, to close the wound with the skin retention element for closure, while the housing remains placed on the patient's skin.

3. The biopsy sampling instrument of claim 2, wherein the skin retention element for closure is one of an absorbable suture staple, a medical grade glue and a cauterant.

4. The biopsy sampling instrument of claim 3, wherein the skin retention element for closure comprises a suture staple of a maximum width less than a diameter of the aperture whereby the wound closure dispenser holds the suture staple and carries the suture staple through the aperture for closure application to the wound and wherein the staple is barbed and has a configuration of one of an s-shape, a helical shape and a three pronged shape relative to the wound.

5. The biopsy sampling instrument of claim 3, wherein the skin retention element for closure is one of a medical grade cyanoacrylate glue and a cauterant contained within an apertured receptacle in the wound closure dispenser and wherein the wound closure dispenser further comprises a fluid dispenser which is configured to dispense one of the cyanoacrylate glue and cauterant on the wound for closure thereof.

6. The biopsy sampling instrument of claim 1, wherein the cutting blade comprises a biopsy punch configured to punch into the biopsy site to circumferentially cut a core sample from the biopsy site and wherein the sample taking member is configured to separate the core sample away from the biopsy site.

7. The biopsy sampling instrument of claim 1, wherein the housing further comprises a marker affixed thereto and configured to mark off the biopsy site for location of anesthetic application to the biopsy site and for biopsy sampling thereof.

8. The biopsy sampling instrument of claim 1, wherein the housing comprises an elongated hand held pen configuration with the aperture located at a terminal end of the elongated pen configuration.

9. The biopsy instrument of claim 8, wherein the housing comprises external manual controls for selectively operating the extending and retracting mechanism and for effecting the anesthetic dispensing and biopsy sampling.

10. A biopsy sampling instrument for use in a dermatological biopsy sampling procedure comprising a hand-held device comprising:
   a) a hand held elongated pen shaped housing optionally having a marker integrated therewith an external end thereof configured for marking off of a selected skin biopsy site;
   b) an anesthetic containing syringe with a dispensing needle within the housing, the syringe being configured for dispensing an anesthetic within the selected skin biopsy site on a patient's skin,
   c) a biopsy sample taking blade within the housing configured for cutting a biopsy sample from the selected and anesthetized biopsy site,
   d) sample taking member within the housing configured to separate the cut biopsy sample from the biopsy site; and
   e) a biopsy wound closure dispenser within the housing configured to dispense a skin closure element to effect a closure of a wound, at the biopsy site, caused by the taking of the biopsy sample;

wherein the housing has an aperture therein adapted to be placed into direct contact against the patient's skin peripheral to the biopsy site and wherein the instrument comprises an extension and retraction mechanism configured to enable the anesthetic dispensing syringe, biopsy sample taking blade, sample taking member and wound closure dispenser to be alternately brought from an offset position relative to the aperture into proximate position relative to the selected biopsy site and extension through the aperture, to alternately and sequentially provide an anesthetic to the selected biopsy site and to cut a biopsy sample from the anesthetized biopsy site, to separate the cut biopsy sample from the skin biopsy site and to effect closure of the wound respectively, without removal of the housing from contact with the biopsy site.

11. The biopsy sampling instrument of claim 10, wherein the extension and retraction mechanism is further configured to alternately laterally move the syringe, biopsy taking blade, and sample taking member out of the longitudinally common path to further enable the wound closure dispenser to be alternately brought into proximate position relative to the wound through the aperture to close the wound with the skin closure element.

12. The biopsy sampling instrument of claim 11, wherein the skin closure element comprises a suture staple of a maximum width less than a diameter of the aperture whereby the wound closure dispenser holds the suture staple and carries the suture staple through the aperture for closure application to the wound and wherein the staple is barbed and has a configuration of one of an s-shape, a helical shape and a three pronged shape.

13. The biopsy sampling instrument of claim 11, wherein the skin closure element is one of a medical grade cyanoacrylate glue and a cauterant contained within an apertured receptacle in the wound closure dispenser and wherein the wound closure dispenser is configured to dispense one of the cyanoacrylate glue and cauterant on the wound for closure thereof.

14. The biopsy sampling instrument of claim 11, wherein the biopsy sample taking blade comprises a biopsy coring punch with an impelling element which is configured to punch the biopsy coring punch into the biopsy site to cut a core sample from the biopsy site and wherein the biopsy sampling blade further comprises the sample taking member.

15. The biopsy sampling instrument of claim 11, wherein the biopsy sample taking blade member comprises a biopsy scraping blade.

16. A method for obtaining a dermatological biopsy sample from a patient's skin, comprising the steps of:

a) identifying a selected biopsy sampling site;

b) placing the aperture of the hand-held instrument of claim 10 in direct proximate contact with the selected biopsy sampling site;

c) extending the anesthetic containing syringe through the aperture and injecting the selected biopsy site with the anesthetic;

d) without removal of the instrument from the selected biopsy site, retracting the syringe through the aperture and moving the syringe to a position laterally offset relative to the aperture and moving the biopsy sample taking blade out of an offset position relative to the aperture for extension through the aperture and cutting of a biopsy skin sample from the anesthetized biopsy site;

e) separating the cut biopsy skin sample from the biopsy sampling site;

f) retaining the biopsy skin sample for sample removal from the instrument; and g) retracting the biopsy sample taking blade through the aperture and moving the biopsy sample taking blade to a position offset relative to the aperture and moving the biopsy wound closure out of an offset position relative to the aperture and extending the biopsy wound closure dispenser through the aperture and closing the biopsy wound.

* * * * *